United States Patent [19]
Runge

[11] Patent Number: 5,437,601
[45] Date of Patent: Aug. 1, 1995

[54] BLOOD CONDUIT AND PULSATILE CARDIOPULMONARY BYPASS PUMP SYSTEM

[76] Inventor: Thomas M. Runge, 2630 Exposition Blvd., Austin, Tex. 78703

[21] Appl. No.: 197,877

[22] Filed: Feb. 17, 1994

Related U.S. Application Data

[63] Continuation-in-part of Ser. No. 845,017, Mar. 2, 1992, Pat. No. 5,300,015.

[51] Int. Cl.$^6$ .............................................. A61M 1/10
[52] U.S. Cl. ........................................ 600/16; 623/3
[58] Field of Search ................ 128/DIG. 12, DIG. 3; 600/16, 17; 623/3

[56] References Cited

U.S. PATENT DOCUMENTS

| | | | |
|---|---|---|---|
| 4,080,958 | 3/1978 | Bregman et al. | 600/16 |
| 4,143,425 | 3/1979 | Runge | 623/3 |
| 4,250,872 | 2/1981 | Tamari | 600/16 |
| 4,293,961 | 10/1981 | Runge | 623/3 |

Primary Examiner—Lee S. Cohen
Assistant Examiner—Jeffrey R. Jastrzab
Attorney, Agent, or Firm—Brady, O'Boyle & Gates

[57] ABSTRACT

A valveless blood conduit for pulsatile cardiopulmonary bypass pump constructed and arranged to provide a surge chamber, a pumping chamber and a reservoir portion, externally valved for use in a pre-load responsive pulsatile pump. The blood conduit precludes the necessity of employing a large volume venous reservoir in a cardiopulmonary bypass system employing a pre-load responsive pump, thus reducing a patient's blood to exposure to large air-blood interfaces and large non-endothelial surface areas.

3 Claims, 4 Drawing Sheets

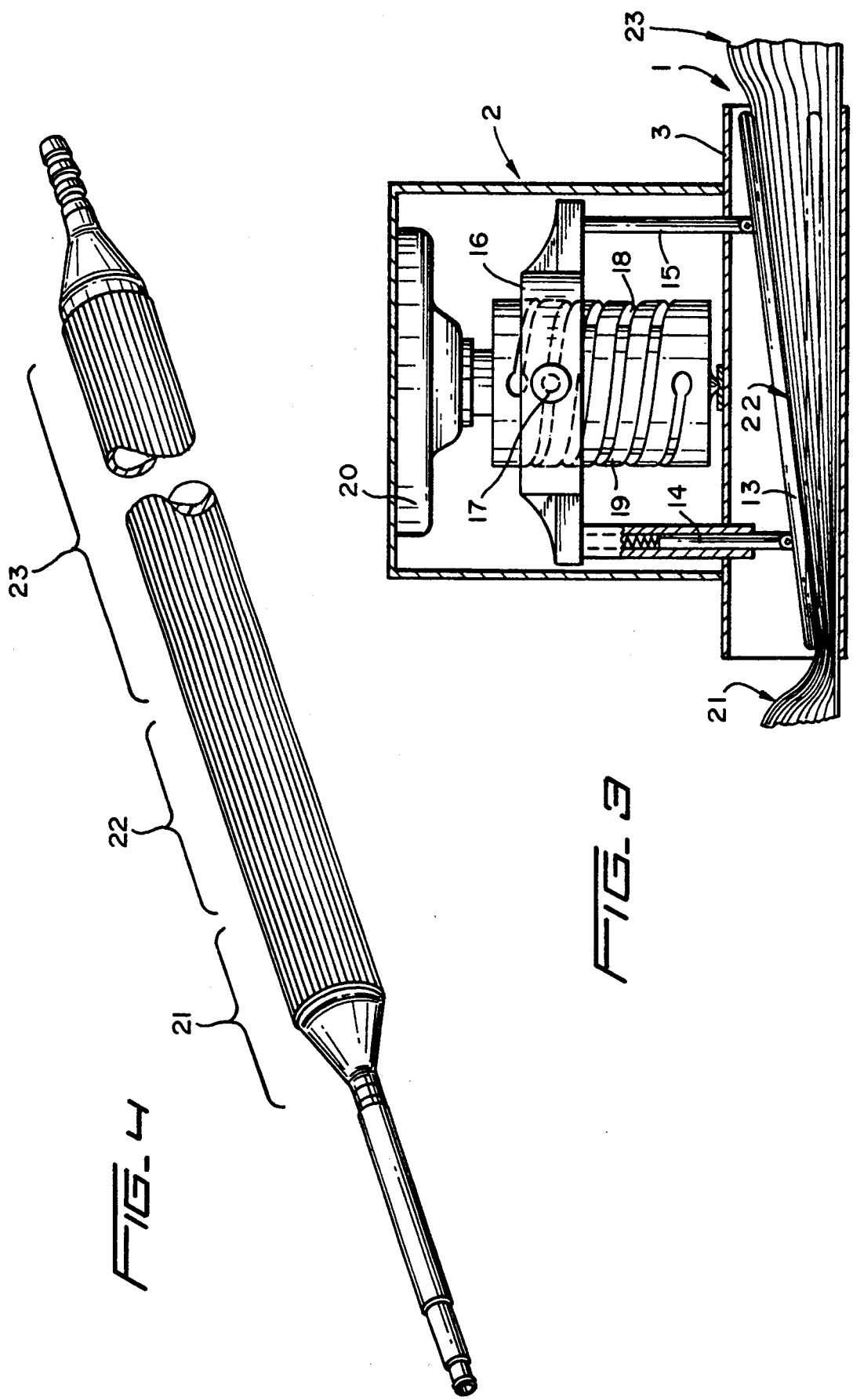

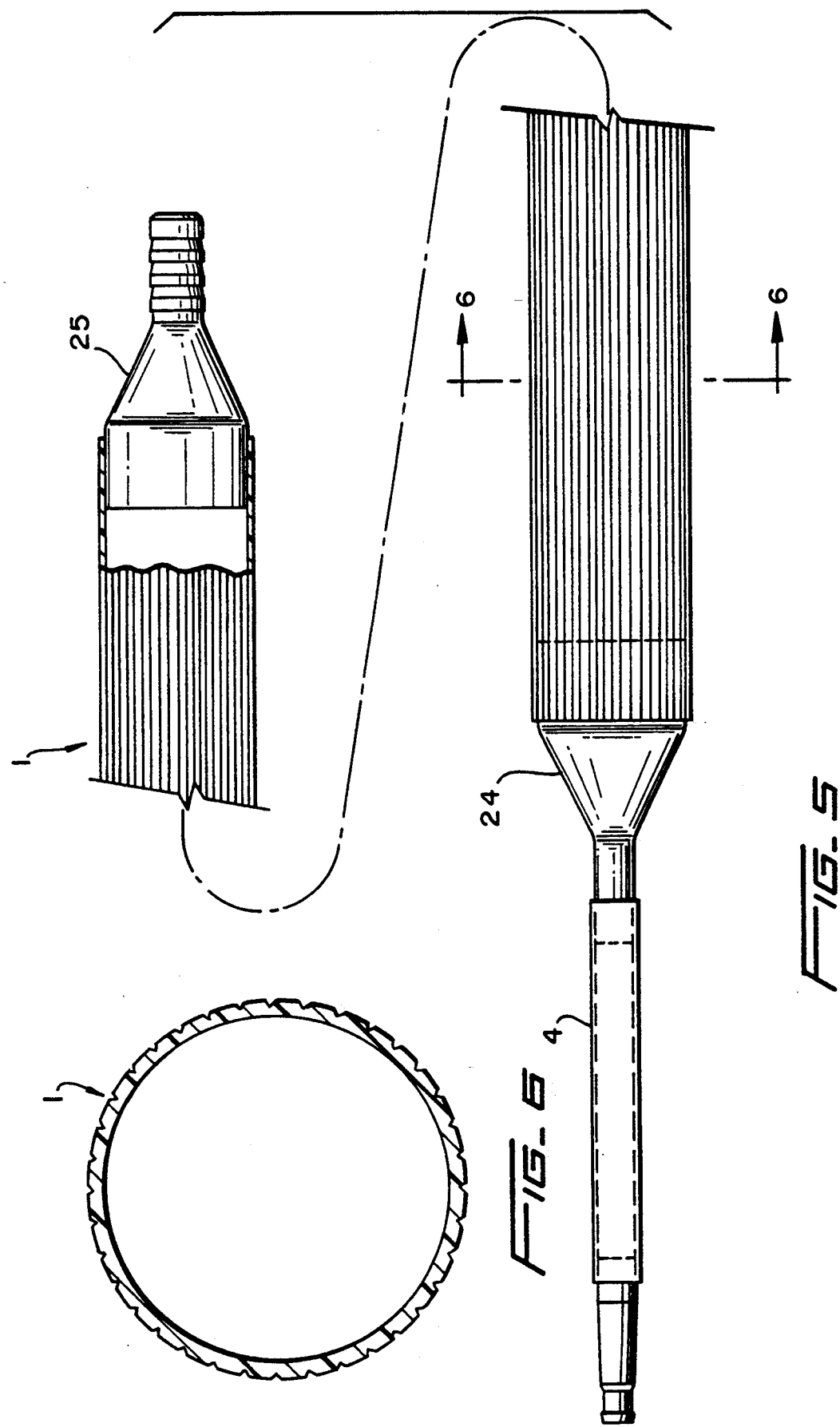

… …

BLOOD CONDUIT AND PULSATILE CARDIOPULMONARY BYPASS PUMP SYSTEM

CROSS-REFERENCE TO RELATED APPLICATION

This is a continuation-in-part application of patent application Ser. No. 07/845,017, filed Mar. 2, 1992 now U.S. Pat. No. 5,300,015.

BACKGROUND OF THE INVENTION

In conventional cardiopulmonary bypass systems, blood is taken from the patient's right atrium and passed through an oxygenator and pumped back into the aorta, thus bypassing the patient's heart and lungs. A blood pump, filters and reservoirs are all included in the system. Large volume venous reservoirs are placed in the blood flow circuit between the right atrium and the inlet to conventional roller or centrifugal cardiopulmonary bypass pumps. While these systems have been commonly employed for years, they are causing problems to patients with regard to brain oxygenation. There are two reasons for this: (1) the roller and centrifugal pumps cannot produce physiologic pulsatile flow, necessary for the brain and other vital organs, and (2) the large venous reservoirs cause hemodilution, thereby diminishing the oxygen carrying capacity per unit of blood. The use of large venous reservoirs increases the cost of the system as well as traumatizing the blood through induction of a large air-blood interface and exposure of blood to large non-endothelial surfaces. Also, increased priming volume, usually a crystalloid solution, is needed when large reservoirs are employed, resulting in dilution and diminished oxygen carrying capacity of the patient's blood.

SUMMARY OF THE INVENTION

To preclude the necessity of employing a large volume venous reservoir in a cardiopulmonary bypass system, the blood conduit of the present invention has been devised to replace the conventional large volume venous reservoir. The blood conduit of the present invention is designed for use with a pulsatile pump of the types disclosed in U.S. Pat. Nos. 4,293,961 and 4,553,532, and comprises, essentially, a tube of biocompatible polymer such as PELLETHANE ® manufactured by Dow, Inc., or polyvinyl chloride and the like. The conduit has no internal valves and is provided with a smooth interior wall. The conduit is cylindrical having a 3.5 cm diameter and a length of 70 cm tapering to 12.5 mm at each end for connection to standard cardiopulmonary bypass tubing. The conduit is dimensioned to form a surge chamber portion 8 cm in length, a compression chamber portion 22 cm in length and a reservoir portion 40 cm in length to thereby supply stroke volume, 45 to 65 ml per stroke, adequate and optimal for a medium sized adult. For a very large adult, a diameter of 4.5 cm instead of 3.5 cm is more physiologic, and for a small adult, or child, a diameter of 2.5 to 3.0 cm. The conduit is disposable and supplied to the retailer in diameters suitable to patient weight, and or body surface area.

BRIEF DESCRIPTION OF THE DRAWINGS

FIG. 3 is a sectional side elevational view of a pulsatile pump employed in the systems of FIGS. 1 and 2;

FIG. 4 is a perspective view of the conduit of the present invention;

FIG. 5 is a fragmentary, sectional side elevational view of the conduit shown in FIG. 4; and FIG. 6 is a view taken along line 6—6 of FIG. 5.

DESCRIPTION OF THE PREFERRED EMBODIMENT

Figure 1:
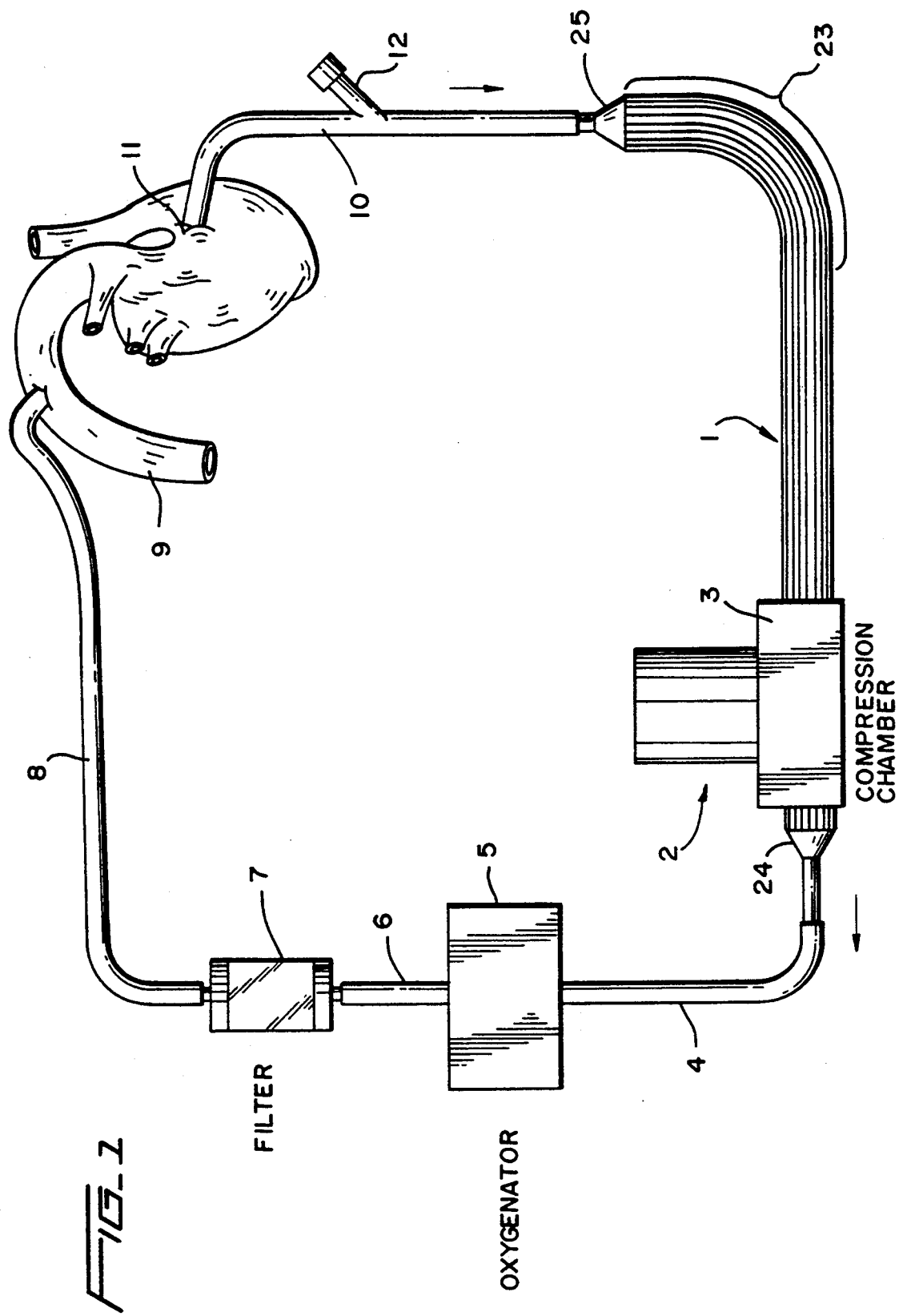
FIG. 1 is a diagrammatic view of a cardiopulmonary bypass system incorporating the conduit of the present invention and showing an oxygenator positioned on the outlet side of a pulsatile pump.

Referring to the drawings, and more particularly to FIG. 1, the conduit 1 of the present invention is adapted for use in a cardiopulmonary bypass system comprising a pre-load responsive pulsatile pump 2 having a compression chamber 3 through which the conduit 1 extends. The pulsatile pump 2 pumps blood from the conduit 1 through a tube 4 connected to an oxygenator 5. The oxygenated blood flows from the oxygenator 5 through a line 6 to a filter 7. The oxygenated, filtered blood then flows through line 8 to the aorta 9 of the patient's heart. The blood then flows through a vertical tube 10 having one end connected to the heart right atrium 11 and the other end connected to the inlet to the conduit 1. The tube 10 includes a port 12 for sampling the blood and adding medication fluids and blood to the flow circuit, or to function as a bubble trap for removing inadvertent in-line air as from atrial tear or other source.

Figure 2:
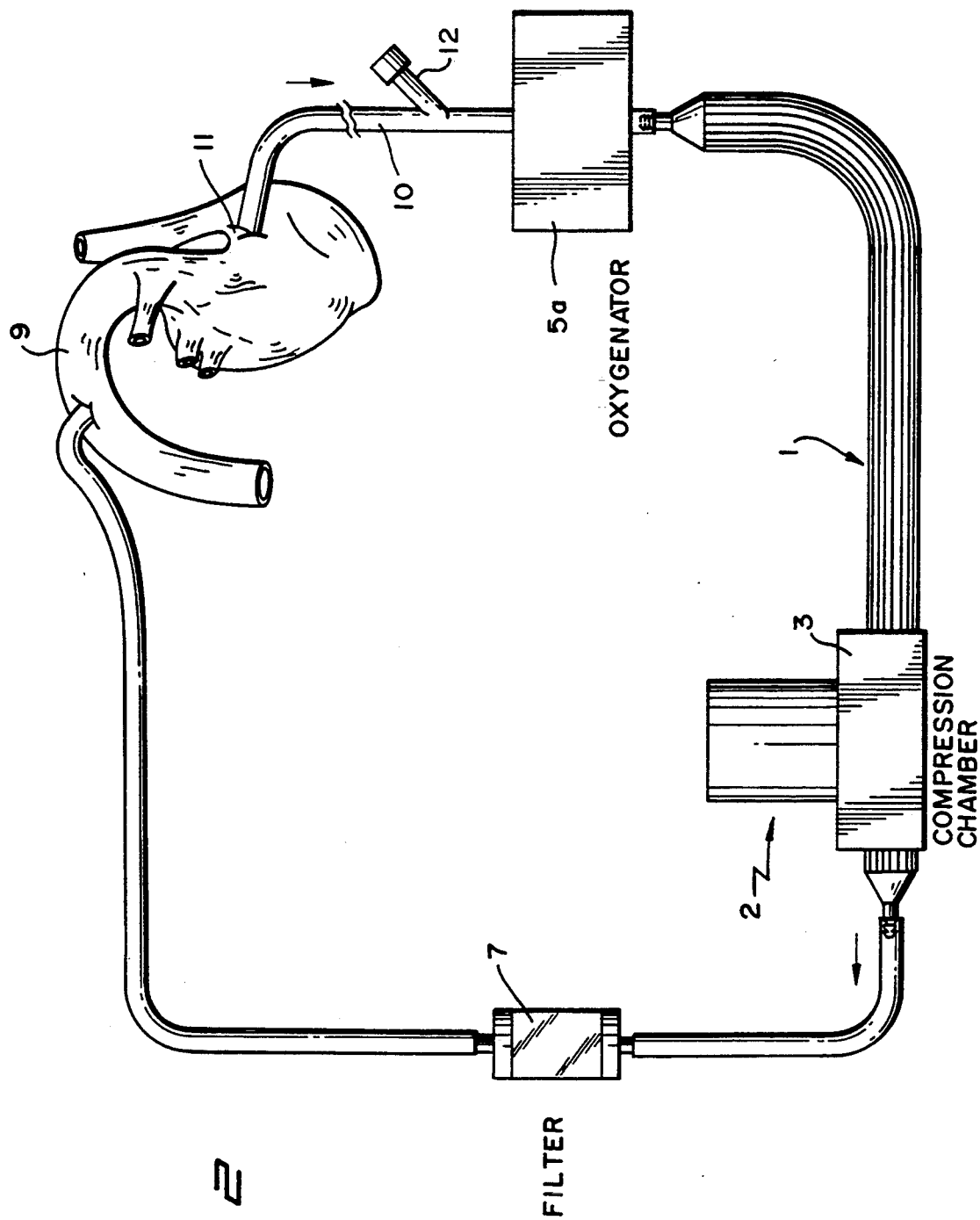
FIG. 2 is a view similar to FIG. 1 but showing the oxygenator positioned on the inlet side of the pump.

The system shown in FIG. 2 is similar to that of Figure; however, the oxygenator 5a is placed in the blood flow circuit at the inlet end of the conduit 1 rather than at the outlet end as shown in FIG. 1, whereby a gravity flow membrane or other oxygenator can be employed.

The pulsatile pump 2, shown in FIG. 3, is of the general type disclosed in applicant's U.S. Pat. No. 4,143,425 or its modified configurations and includes a compression plate 13 positioned within the compression chamber 3 and engaging the exterior wall surface of the conduit 1, the pump's ventricle. A pair of legs 14 and 15 connect the compression plate 13 to a ring 16 having a follower pin 17 engaged within a helical groove 18 formed in a shaft 19 driven by a motor 20. Rotation of the shaft 19 will result in axial movement of the ring 16 thereon causing the plate 13 to compress the conduit in a manner disclosed in U.S. Pat. No. 4,143,425.

When using the pulsatile pump 2, since the conduit 1 is valveless, inlet and outlet valves would be external of the conduit 1 and be pinch type as disclosed in U.S. Pat. No. 4,553,532.

The details of the construction of the blood conduit 1 are illustrated in FIGS. 4, 5 and 6, wherein the blood conduit includes a surge chamber portion 21, a pumping chamber portion 22 and a reservoir portion 23, the pumping chamber portion 22 being positioned under the compression plate 13 of the pump 2 to form the ventricular portion of the conduit, as shown in FIG. 3, while the surge portion or chamber 21, which enhances the closure of the exit valve of the ventricular portion of the conduit, is positioned to the left of the pump and the reservoir portion 23 is positioned to the right of the pump. The blood conduit comprises a cylindrical tube of biocompatible polymer, such as, PELLETHANE ®, manufactured by Dow, Inc., or polyvinyl chloride, or the like. The conduit has no interior valves and is provided with a smooth interior wall. The conduit has a diameter of 3.5 cm, a wall thickness of 25 mils, and a length of 70 cm tapering at each end, as at 24 and 25 to 12.5 mm for connection to the standard cardiopulmonary bypass tubing as shown in FIGS. 1 and 2. The conduit is dimensioned so that the surge chamber portion 21 has a length of 8 cm; the compression or pumping chamber portion 22 has a length of 22 cm, and the reservoir portion 23 has a length of 40 cm, to thereby supply stroke volume, 45 to 65 ml per stroke, adequate and optimal for a medium sized adult. While the tapered ends 24 and 25 are illustrated as separate components providing adapters for connection to the bypass tubing, the conduit 1 and adapters 24 and 25 can be molded in a single integral unit.

When connected into the system as shown in FIG. 1, the portion 23 of the conduit provides a blood reservoir for the pump 2, and the tube 10 provides a vertical portion for enhancing the blood flow velocity and volume into the reservoir portion 23.

From the above description, it will be appreciated by those skilled in the art that the construction and arrangement of the blood conduit of the present invention precludes the necessity of employing additional reservoirs in the system, whereby there is a direct connection from the atrium to the pre-load responsive pulsatile pump, thereby allowing the pump to be more responsive to atrial volume. By employing a pre-load responsive pump, a physiologic morphology pulsatile flow of blood is capable of being delivered into humans through standard size aortic cannulas.

It is to be understood that the form of the invention herewith shown and described is to be taken as a preferred example of the same, and that various changes in the shape, size and arrangement of parts may be resorted to without departing from the spirit of the invention or scope of the subjoined claims.

I claim:

1. A cardiopulmonary bypass system comprising in combination a valveless blood conduit and a pulsatile cardiopulmonary bypass pump, said pump having an inlet end, an outlet end a compression chamber between said inlet end and said outlet end, and a compression plate having a first end portion and a second end portion in said compression chamber, said conduit extending through the inlet end, underneath said compression plate in said compression chamber and outwardly of the outlet end of the bypass pump, said conduit comprising a disposable tube of biocompatible polymer having a smooth internal wall and dimensioned to provide a surge chamber positioned at the outlet end of said pump, a reservoir portion positioned at the inlet end of said pump, and a pumping chamber portion positioned in the compression chamber of said pump, said conduit having a diameter of 3.5 cm, the surge chamber extending from the first end portion of said compression plate a length of 8 cm, the pumping chamber portion extending between the first and second end portions of said compression plate a length of 22 cm and the reservoir portion extending from the second end portion of the compression plate a length of 40 cm, whereby adequate and optimal stroke volume is supplied to a medium sized adult patient, without employing large venous reservoirs in the system, thereby diminishing hemodilution and the exposure of blood to air and to non-endothelized surfaces, while the blood is transmitted to the patient through a smooth walled, valveless bypass system.

2. A cardiopulmonary bypass system comprising in combination a valveless blood conduit and a pulsatile cardiopulmonary bypass pump, said pump having an inlet end, an outlet end a compression chamber between said inlet end and said outlet end, and a compression plate having a first end portion and a second end portion in said compression chamber, said conduit extending through the inlet end, underneath said compression plate in said compression chamber and outwardly of the outlet end of the bypass pump, said conduit comprising a disposable tube of biocompatible polymer having a smooth internal wall and dimensioned to provide a surge chamber positioned at the outlet end of said pump, a reservoir portion positioned at the inlet end of said pump, and a pumping chamber portion positioned in the compression chamber of said pump, said conduit having a diameter of 4.5 cm, the surge chamber portion extending from the first end of said compression plate a length of 8 cm, the pumping chamber portion extending between the first and second end portions of said compression plate a length of 22 cm, and the reservoir portion extending from the second end portion of the compression plate a length of 40 cm, whereby adequate and optimal stroke volume is supplied to a large sized adult patient, without employing large venous reservoirs in the system, thereby diminishing hemodilution and the exposure of blood to air and to non-endothelized surfaces, while the blood is transmitted to the patient through a smooth walled, valveless bypass system.

3. A cardiopulmonary bypass sytsem comprising in combination a valveless blood conduit and a pulsatile cardiopulmonary bypass pump, said pump having an inlet end, an outlet end a compression chamber between said inlet end and said outlet end, and a compression plate having said first end portion and a second end portion in a compression chamber, said conduit extending through the inlet end, underneath said compression plate in said compression chamber and outwardly of the outlet end of the bypass pump, said conduit comprising a disposable tube of biocompatible polymer having a smooth internal wall and dimensioned to provide a surge chamber positioned at the outlet end of said pump, a reservoir portion positioned at the inlet end of said pump, and a pumping chamber portion positioned in the compression chamber of said pump, said conduit having a diameter of between 2.5 and 3.0 cm, the surge chamber extending from the first end portion of said compression plate a length of 8 cm, the pumping chamber portion extending between the first and second end portions of said compression plate a length of 22 cm and the reservoir portion extending from the second end portion of the compression plate a length of 40 cm, whereby adequate and optimal stroke volume is supplied to a small adult or child patient, without employing large venous reservoirs in the system, thereby diminishing hemodilution and the exposure of blood to air and to non-endothelized surfaces, while the blood is transmitted to the patient through a smooth walled, valveless bypass system.

* * * * *